(12) United States Patent
Scholz et al.

(10) Patent No.: US 8,372,051 B2
(45) Date of Patent: Feb. 12, 2013

(54) MEDICAL DRESSING WITH EDGE PORT AND METHODS OF USE

(75) Inventors: Matthew T. Scholz, Woodbury, MN (US); David R. Holm, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 205 days.

(21) Appl. No.: 12/811,033

(22) PCT Filed: Dec. 23, 2008

(86) PCT No.: PCT/US2008/088092
§ 371 (c)(1),
(2), (4) Date: Jun. 28, 2010

(87) PCT Pub. No.: WO2009/088757
PCT Pub. Date: Jul. 16, 2009

(65) Prior Publication Data
US 2010/0286639 A1    Nov. 11, 2010

Related U.S. Application Data

(60) Provisional application No. 61/017,957, filed on Dec. 31, 2007.

(51) Int. Cl.
*A61F 13/02* (2006.01)
*A61M 1/00* (2006.01)
(52) U.S. Cl. ........ 604/319; 604/289; 604/290; 604/304; 604/305; 604/306; 604/307; 604/308; 602/41
(58) Field of Classification Search .............. 602/41–79; 604/289, 290, 304–308
See application file for complete search history.

(56) References Cited

U.S. PATENT DOCUMENTS

| 2,896,618 | A | 7/1959 | Schaefer |
| RE24,906 | E | 12/1960 | Ulrich |
| 3,389,827 | A | 6/1968 | Abere |
| D215,566 | S | 10/1969 | Gilson |
| 3,645,835 | A | 2/1972 | Hodgson |
| 3,761,211 | A | 9/1973 | Parkinson |
| 3,874,387 | A | 4/1975 | Barbieri |
| 3,884,606 | A | 5/1975 | Schrenk |
| 3,924,990 | A | 12/1975 | Schrenk |

(Continued)

FOREIGN PATENT DOCUMENTS

| DE | 10 2008 020554 A1 | 10/2008 |
| EP | 0 051 935 | 5/1982 |

(Continued)

OTHER PUBLICATIONS

U.S. Appl. No. 61/042,338, Scholz, filed Apr. 4, 2008.

(Continued)

*Primary Examiner* — Melanie Hand
*Assistant Examiner* — Andrew S Lo
(74) *Attorney, Agent, or Firm* — Kenneth B. Wood (57) ABSTRACT

Medical dressings and medical dressing kits that can be used to provide a ported medical dressing for placement over a wound or other body site where controlled fluid access is desired. The controlled fluid access provided by the medical dressings may be useful to remove fluids from the wound (as in, e.g., negative or reduced pressure therapies), to provide one or more gases to a wound site, to provide one or more liquids to a wound site, and/or to provide one or more active agents to a wound site. To achieve controlled fluid access, the medical dressing and medical dressing kits may include a port body with a lower surface that is adhesively adhered to the skin at the periphery of a wound or other body site.

35 Claims, 3 Drawing Sheets

U.S. PATENT DOCUMENTS

| | | |
|---|---|---|
| 4,112,213 A | 9/1978 | Waldman |
| 4,310,509 A | 1/1982 | Berglund et al. |
| 4,322,877 A | 4/1982 | Taylor |
| 4,323,557 A | 4/1982 | Rosso et al. |
| 4,328,441 A | 5/1982 | Kroeger, Jr. |
| 4,330,730 A | 5/1982 | Kurz |
| 4,398,910 A | 8/1983 | Blake |
| 4,405,402 A | 9/1983 | Quilliam |
| 4,472,480 A | 9/1984 | Olson |
| 4,485,809 A | 12/1984 | Dellas |
| 4,499,896 A | 2/1985 | Heinecke |
| 4,541,426 A | 9/1985 | Webster |
| 4,569,674 A | 2/1986 | Phillips et al. |
| 4,595,001 A | 6/1986 | Potter et al. |
| 4,598,004 A | 7/1986 | Heinecke |
| 4,600,001 A | 7/1986 | Gilman |
| 4,606,871 A | 8/1986 | Krueger |
| 4,627,138 A | 12/1986 | Im |
| 4,664,106 A | 5/1987 | Snedeker |
| 4,737,410 A | 4/1988 | Kantner |
| 4,743,232 A | 5/1988 | Kruger |
| 4,778,446 A | 10/1988 | Jensen |
| 4,820,586 A | 4/1989 | Krueger |
| 4,969,880 A | 11/1990 | Zamierowski |
| 5,088,483 A | 2/1992 | Heinecke |
| 5,100,396 A | 3/1992 | Zamierowski |
| 5,153,859 A | 10/1992 | Chatigny |
| 5,160,315 A | 11/1992 | Heinecke et al. |
| 5,160,322 A | 11/1992 | Scheremet |
| 5,261,893 A | 11/1993 | Zamierowski |
| D347,058 S | 5/1994 | Valentine |
| 5,478,333 A | 12/1995 | Asherman, Jr. |
| 5,527,293 A | 6/1996 | Zamierowski |
| 5,531,855 A | 7/1996 | Heinecke et al. |
| 5,622,711 A | 4/1997 | Chen |
| 5,633,010 A | 5/1997 | Chen |
| 5,783,120 A | 7/1998 | Ouderkirk |
| 5,803,086 A | 9/1998 | Scholz et al. |
| 5,825,543 A | 10/1998 | Ouderkirk et al. |
| D409,754 S | 5/1999 | Dunshee |
| 5,979,450 A | 11/1999 | Baker et al. |
| 5,997,800 A | 12/1999 | Wimberger Friedl |
| 6,071,267 A | 6/2000 | Zamierowski |
| D430,674 S | 9/2000 | Dunshee |
| 6,143,216 A | 11/2000 | Loch et al. |
| 6,169,224 B1 | 1/2001 | Heinecke et al. |
| D437,217 S | 2/2001 | Bloor |
| 6,264,976 B1 | 7/2001 | Heinecke et al. |
| D454,955 S | 3/2002 | Dunshee |
| 6,420,622 B1 | 7/2002 | Johnston et al. |
| 6,436,432 B2 | 8/2002 | Heinecke |
| D465,572 S | 11/2002 | Dunshee |
| D473,947 S | 4/2003 | Jacobson |
| 6,539,691 B2 | 4/2003 | Beer |
| 6,607,764 B1 | 8/2003 | Keller |
| 6,685,682 B1 | 2/2004 | Heinecke et al. |
| 6,733,803 B1 | 5/2004 | Vidkjaer |
| 6,742,522 B1 | 6/2004 | Baker et al. |
| D493,230 S | 7/2004 | Liedtke |
| 6,867,342 B2 | 3/2005 | Johnston et al. |
| 6,893,655 B2 | 5/2005 | Flanigan et al. |
| 6,913,803 B2 | 7/2005 | Peper |
| 6,933,051 B2 | 8/2005 | Fleming et al. |
| 6,949,283 B2 | 9/2005 | Kollaja et al. |
| 6,994,904 B2 | 2/2006 | Joseph et al. |
| 7,179,245 B2 | 2/2007 | Glori |
| 7,183,454 B1 | 2/2007 | Rosenberg |
| 7,214,217 B2 | 5/2007 | Pedersen et al. |
| 7,216,651 B2 | 5/2007 | Argenta |
| D557,413 S | 12/2007 | Buermann |
| 7,361,184 B2 | 4/2008 | Joshi |
| 7,429,687 B2 | 9/2008 | Kauth |
| D612,504 S | 3/2010 | Ha |
| 7,777,397 B2 | 8/2010 | Bharti |
| D629,910 S | 12/2010 | Ha |
| D629,911 S | 12/2010 | Ha |
| 2002/0082540 A1 | 6/2002 | Johnston |
| 2003/0006669 A1 | 1/2003 | Pei et al. |
| 2003/0007038 A1 | 1/2003 | Nakatani |
| 2003/0097100 A1 | 5/2003 | Watson |
| 2003/0153965 A1 | 8/2003 | Supronowicz |
| 2004/0073151 A1 | 4/2004 | Weston |
| 2004/0109236 A1 | 6/2004 | Nishioka |
| 2004/0243073 A1 | 12/2004 | Lockwood |
| 2005/0046030 A1 | 3/2005 | Nakamura |
| 2005/0089539 A1 | 4/2005 | Scholz et al. |
| 2006/0051384 A1 | 3/2006 | Scholz et al. |
| 2006/0051385 A1 | 3/2006 | Scholz |
| 2006/0052452 A1 | 3/2006 | Scholz |
| 2006/0147701 A1 | 7/2006 | Lockridge |
| 2007/0156075 A1 | 7/2007 | Heinecke |
| 2007/0172157 A1 | 7/2007 | Buchman |
| 2007/0209326 A1 | 9/2007 | Tretina |
| 2007/0233022 A1 | 10/2007 | Henley |
| 2008/0033377 A1 | 2/2008 | Kauth |
| 2010/0318052 A1 | 12/2010 | Ha |

FOREIGN PATENT DOCUMENTS

| | | |
|---|---|---|
| JP | 8-276537 | 10/1996 |
| JP | 2000-127176 | 5/2000 |
| WO | WO 93/09727 A | 5/1993 |
| WO | WO 02/096647 A1 | 12/2002 |
| WO | WO 2006/118059 A1 | 11/2006 |
| WO | WO 2007/030601 | 3/2007 |
| WO | WO 2008/014358 | 1/2008 |
| WO | WO 2008/019310 | 2/2008 |
| WO | WO 2008/041926 | 4/2008 |

OTHER PUBLICATIONS

U.S. Appl. No. 61/017,957, Scholz, filed Dec. 31, 2007.
U.S. Appl. No. 61/042,698, Bharti, filed Apr. 4, 2008.
U.S. Appl. No. 12/936,255, Bharti, filed Apr. 1, 2009.
U.S. Appl. No. 12/936,273, Scholz, filed Apr. 1, 2009.
Yoon, C-B., et al., "Multilayer Bender-Type PZT-PZN Actuator by Co-Extrusion Process," Journal of the European Ceramic Society, vol. 26 (2006) pp. 2345-2348.
*Handbook of Pressure Sensitive Adhesive Technology*, Van Nostrand-Reinhold, 1982, pp. 384-403, chapter 18.
International Search Report, PCT/US2010/038595, Jul. 30, 2010, 3 Pages.
Written Opinion of the International Searching Authority, PCT/US2010/038595, Jul. 30, 2010, 6 Pages.
International Search Report, PCT/US2008/088092, Mar. 27, 2009, 6 Pages.
Written Opinion of the International Searching Authority, PCT/US2008/088092, Mar. 27, 2009, 12 Pages.
International Search Report, PCT/US2008/052900, Jul. 28, 2008, 3 Pages.
Written Opinion of the International Searching Authority, PCT/US2008/052900, Jul. 28, 2008, 3 Pages.
International Search Report, PCT/US2009/039058, Jul. 9, 2009, 4 pages.
Written Opinion of the International Searching Authority, PCT/US2009/039058, Jul. 9, 2009, 6 pages.
International Search Report, PCT/US2009/039149, May 13, 2009, 3 pages.
Written Opinion of the International Searching Authority, PCT/US2009/039149, May 13, 2009, 7 pages.

MEDICAL DRESSING WITH EDGE PORT AND METHODS OF USE

CROSS REFERENCE TO RELATED APPLICATIONS

This application is a national stage filing under 35 U.S.C. 371 of PCT/US2008/088092, filed Dec. 23, 2008, which claims priority to U.S. Provisional Application No. 61/017,957, filed Dec. 31, 2007, the disclosures of which are incorporated by reference in their entirety herein.

Dressings adapted for use with negative pressure wound therapy (such as those described in, e.g., U.S. Pat. Nos. 4,969,880; 5,261,893; 5,527,293; and 6,071,267 (all to Zamierowski)) often have constructions that can compromise the sterility of the wound over which they are placed. These products introduce a tube or wound drain either through a multi-piece dressing or under a single piece dressing. In either case, it is difficult (if not impossible) to obtain a good seal and, during treatment, air can leak into the wound. That air can carry contamination into the wound and/or impair the effectiveness of the pressure-based therapy.

Similar issues may be experienced when attempting to provide oxygen therapy to wounds. In particular, it may be difficult to obtain a sealed environment to which oxygen can be delivered to a wound site without compromising the barrier properties of a dressing located over the wound.

SUMMARY

The present invention provides medical dressings and medical dressing kits that can be used to provide a ported medical dressing for placement over a wound or other body site where controlled fluid access is desired. That fluid access is preferably available without removing or otherwise disturbing the medical dressing. In particular, the controlled fluid access provided by medical dressings of the present invention may be useful to remove fluids from the wound (as in, e.g., negative or reduced pressure therapies), to provide one or more gases (e.g., oxygen, nitric oxide, ozone, etc.) to a wound site, to provide one or more liquids (e.g., saline, etc.), and/or to provide one or more active agents (e.g., carried in a liquid or gas) to a wound site.

To achieve controlled fluid access, the medical dressing and medical dressing kits of the present invention preferably include a port body with a lower surface that is adhesively adhered to the skin at the periphery of a wound or other body site. The port body also includes an upper surface, with the lower surface and the upper surface meeting along tapered edges on at least two opposing sides of the port body. A backing is attached over the upper surface and the skin surrounding the tapered edges of the port body. The tapered shape of the edges allows the backing to follow a relatively smooth transition between the port body and the skin surface. That smooth transition preferably allows the medical dressings of the present invention to provide a repeatable, high integrity seal between the dressing and the skin.

The port body also preferably includes one or more passages formed therethrough, with the passages having external ports that open outside of the dressing and internal ports that open within the interior volume defined by the medical dressing backing and the port body when the medical dressing and port body are secured to the skin surrounding a wound or other body site. With the exception of the passages, it may be preferred that the port bodies are solid or otherwise fluid impermeable such that access to the interior volume is controlled.

In one aspect, the present invention provides a medical dressing that includes a port body with a lower surface and an upper surface, wherein the lower surface and the upper surface meet along two opposing tapered edges, and wherein the upper surface and the lower surface of the port body form an internal angle of less than 90 degrees along the tapered edges of the port body; a passage extending through the upper surface of the port body from an external opening to an internal opening, wherein both the external opening and the internal opening are located in the upper surface; pressure sensitive adhesive located on the lower surface of the port body; and a backing attached to the upper surface of the port body, the backing extending over the upper surface between the two opposing tapered edges of the port body, wherein the external opening is located proximate the edge of the backing such that, when the backing and the lower surface of the port body are attached to a body surface, the internal opening opens into an internal volume defined by the backing, the port body and the body surface.

In another aspect, the present invention provides a medical dressing that includes a port body with a lower surface and an upper surface, wherein the lower surface and the upper surface meet along two opposing tapered edges, wherein the upper surface and the lower surface form an acute internal angle along the tapered edges; a passage extending through the upper surface of the port body from an external opening to an internal opening, wherein both the external opening and the internal opening are located in the upper surface; pressure sensitive adhesive located on the lower surface of the port body; a backing attached to the upper surface of the port body, the backing comprising an edge extending over the upper surface between the two opposing tapered edges of the port body; pressure sensitive adhesive located on a lower face of the backing, wherein the lower face of the backing faces the upper surface of the port body, and wherein the backing is adhesively attached to the upper surface of the port body; and a release liner covering the pressure sensitive adhesive on the lower surface of the port body and the pressure sensitive adhesive on the lower face of the backing; wherein the external opening in the port body is located proximate the edge of the backing that extends over the upper surface of the port body, and wherein the internal opening opens into an internal volume defined by the backing, the port body and the release liner.

The medical dressings may optionally include one or more of the following features: the internal angle formed by the upper surface and the lower surface of the port body along the tapered edges of the port body may be 75 degrees or less; the port body may extend outside of a perimeter of the backing, wherein a portion of the upper surface is not covered by the backing outside of the perimeter of the backing; the upper surface of the port body may include an internal port surface that is exposed within the internal volume, wherein the internal opening is located in the internal port surface; the backing may be adhesively attached to the upper surface the port body; the port body may include an internal extension connected to the internal opening; the port body may include an external extension connected to the external opening; a one-way exhaust valve may be arranged to permit fluid flow through the passage out of the internal volume and to restrict fluid flow through the passage into the internal volume; a feed valve may be arranged to permit fluid flow into the internal volume, and the feed valve may be located within an auxiliary port body. If provided, the auxiliary port body may include a flat lower surface and an upper surface, wherein the lower surface and the upper surface meet along two opposing tapered edges, wherein the upper surface and the lower surface of the auxiliary port body form an internal angle of less than 90 degrees along the tapered edges of the auxiliary port body; a passage extending through the upper surface of the auxiliary port body from an external opening to an internal opening, wherein both the external opening and the internal opening are located in the upper surface; pressure sensitive adhesive located on the lower surface of the auxiliary port body; and wherein the backing is attached to the upper surface of the auxiliary port body, the backing extending over the upper surface between the two opposing tapered edges of the auxiliary port body, wherein the external opening is located proximate the edge of the backing such that, when the backing and the lower surface of the auxiliary port body are attached to a body surface, the internal opening opens into an internal volume defined by the backing, the auxiliary port body and the body surface. Still further optional features, one or more of which may be provided in the medical dressings, may include one or more of the following: the upper surface of the port body may be a curved surface; the upper surface of the port body may be in the form of a section of a circular cylinder; the port body may be a solid body; a secondary passage may be provided that extends through the port body between a secondary external opening and a secondary internal opening, wherein, when the backing and the lower surface of the port body are attached to a body surface, the secondary internal port opens into an internal volume defined by the backing, the port body and the body surface; the backing may be a polymeric film backing; etc.

In another aspect, the present invention may provide a medical dressing kit that includes a port body having a lower surface and an upper surface, wherein the lower surface and the upper surface meet along two opposing tapered edges, wherein the upper surface and the lower surface of the port body form an internal angle of less than 90 degrees along the tapered edges of the port body; and wherein the port body further includes a passage extending through the upper surface of the port body from an external opening to an internal opening, wherein both the external opening and the internal opening are located in the upper surface, and further wherein pressure sensitive adhesive is located on the lower surface of the port body; and an adhesive composite that comprises a backing, pressure sensitive adhesive located on a lower face of the backing, and a release liner covering the pressure sensitive adhesive on the lower face of the backing.

In various embodiments, the medical dressing kits described herein may optionally include one or more of the following features: two or more of the port bodies may be included in the kit; the upper surface and the lower surface of the port body may form an angle of 75 degrees or less along the tapered edges of the port body; the backing comprises a polymeric film backing; wound packing material; a one-way exhaust valve may be provided and arranged to permit fluid flow through the passage from the internal opening to the external opening and to restrict fluid flow through the passage from the external opening to the internal opening; etc.

In another aspect, the present invention may provide a method of treating a wound, the method including: applying a medical dressing over a wound, wherein the medical dressing includes a port body comprising a lower surface and an upper surface, wherein the lower surface and the upper surface meet along two opposing tapered edges, wherein the upper surface and the lower surface of the port body form an internal angle of less than 90 degrees along the tapered edges of the port body; a passage extending through the upper surface of the port body from an external opening to an internal opening, wherein both the external opening and the internal opening are located in the upper surface; pressure sensitive adhesive located on the lower surface of the port body; and a backing attached to the upper surface of the port body, the backing extending over the upper surface between the two opposing tapered edges of the port body, wherein the external opening is located proximate the edge of the backing; wherein the lower surface of the port body is attached to a body surface surrounding the wound, and wherein the internal opening opens into an internal volume defined by the backing, the port body; the body surface, and the wound. The method further includes removing fluid from the internal volume through the passage in the port body.

In various embodiments, the methods may include one or more of the following features: the fluid removed from the internal volume may include air such that the pressure within the internal volume is below atmospheric pressure outside of the internal volume; the fluid removed from the internal volume may include wound exudate from the wound; the medical dressing may include a one-way exhaust valve arranged to permit fluid flow through the passage out of the internal volume and to restrict fluid flow through the passage into the internal volume; the medical dressing may include a feed valve arranged to permit fluid flow into the internal volume and the method may include delivering a selected fluid into the internal volume through the feed valve; the selected fluid delivered through the feed valve may include an active agent. If provided, the feed valve may be located within an auxiliary port body. If provided, the auxiliary port body may include a lower surface and an upper surface, wherein the lower surface and the upper surface meet along two opposing tapered edges, wherein the upper surface and the lower surface of the auxiliary port body form an internal angle of less than 90 degrees along the tapered edges of the auxiliary port body; a passage extending through the upper surface of the auxiliary port body from an external opening to an internal opening, wherein both the external opening and the internal opening are located in the upper surface; pressure sensitive adhesive located on the lower surface of the auxiliary port body; and wherein the backing is attached to the upper surface of the auxiliary port body, the backing extending over the upper surface between the two opposing tapered edges of the auxiliary port body, wherein the external opening is located proximate the edge of the backing such that the internal opening opens into the internal volume.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTIONS OF THE VIEWS OF THE DRAWING

The present invention will be further described with reference to the views of the drawing, wherein.

DESCRIPTION OF EXEMPLARY EMBODIMENTS

In the following description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Figure 1:
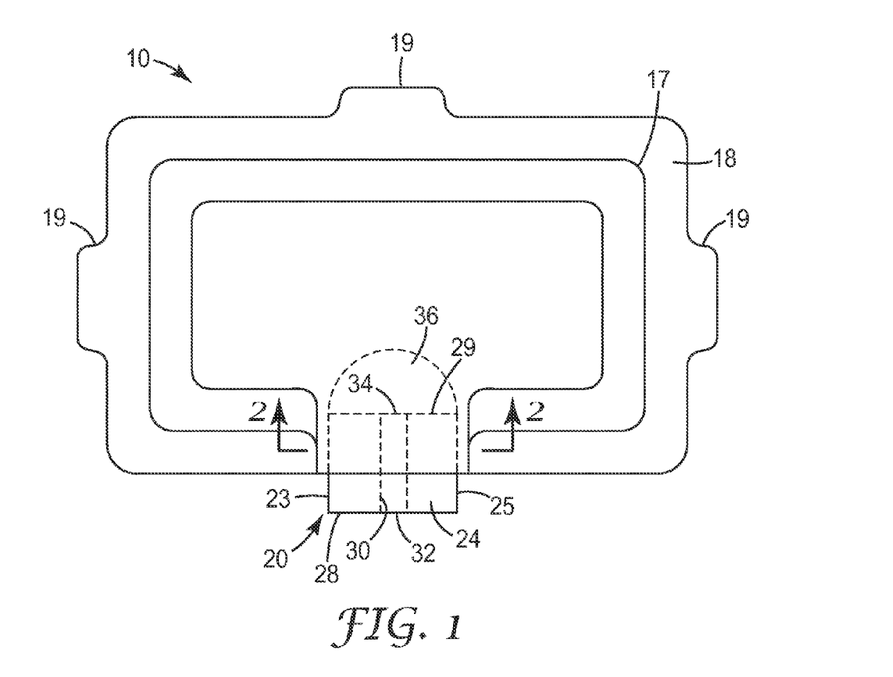
FIG. 1 is a plan view of one embodiment of a medical dressing according to the present invention.
Figure 2:
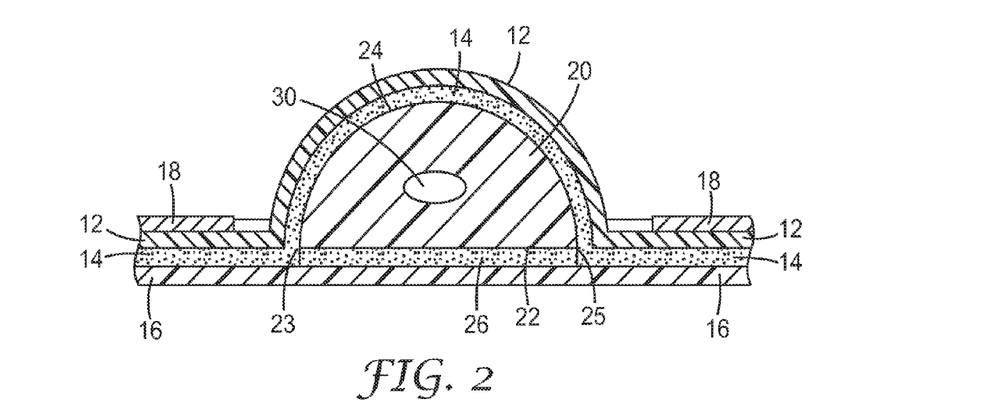
FIG. 2 is an enlarged partial cross-sectional view of the medical dressing of FIG. 1 taken along line 2-2 in FIG. 1.

One exemplary embodiment of a medical dressing according to the present invention is depicted in FIGS. 1 & 2 (where FIG. 2 is a partial cross-sectional view taken along line 2-2 in FIG. 1). The medical dressing 10 includes a backing 12 (which may preferably be conformable as described herein); pressure-sensitive adhesive 14 on a bottom face of the backing 12; a liner 16 attached to the exposed surface of pressure-sensitive adhesive 14; and a carrier 18 attached to the top face of the backing 12.

The dressing 10 further includes a port body 20 located between the liner 16 and the backing 12. The port body 20 includes a lower surface 22 and an upper surface 24. The backing 12 is preferably attached to the upper surface 24 of the port body 20. It may be preferred that the backing 12 be adhesively attached to the upper surface 24 of the port body 20 using the adhesive 14 on the backing 12, although other techniques of attaching the upper surface 24 to the backing 12 may be used in place of or in addition to adhesive 14 (e.g., heat sealing, ultrasonic welding, etc.).

Although the medical dressing includes only one port body 20, it should be understood that medical dressings of the present invention (and kits as described herein) may include more than one port body if additional access to a wound or other body site is desired.

The port body 20 preferably includes adhesive 26 (preferably pressure sensitive adhesive) on its lower surface 22, with the adhesive 26 preferably being covered by the liner 16 that covers the adhesive 14 on the remainder of the backing 12. It may be preferred that the adhesive 26 be the same as the adhesive 14, although this arrangement is not required.

The port body 20 may also preferably include one or more passages 30 formed therethrough. Each passage 30 may preferably include at least one external opening 32 that is located proximate the perimeter of the backing 12 and at least one internal opening 34 that is located within the perimeter of the backing 12.

The port body 20 may preferably include an external port surface 28 and an internal port surface 29 as a part of the upper surface. The external opening 32 of the passage 30 may preferably be located within the external port surface 28 which is, in turn, preferably located outside of the perimeter of the backing 12 (in particular, the external port surface 28 is preferably not covered by the backing 12). The internal opening 34 of the passage 30 may preferably be located in the internal port surface 29 which is, in turn, preferably located within the perimeter of the backing 12.

In use, it may be preferred that the port body 20 support the backing 12 above a surface to which the dressing 10 is attached such that the port body 20 and the backing 12 define an internal volume 36 into which the internal opening 34 opens. In one manner, the port body 20 may be described as causing the backing 12 to "tent" above the surface to which the dressing 10 is attached. As such, passage 30 opens into the internal volume 36 through the passage 30. In the embodiment depicted in FIG. 1, the internal volume is created between the backing 12 and the underlying liner 16. In use over a wound, the port body 20 and the backing 12 will form an internal volume above the wound that is covered by the dressing 10 (which may be considered to be liner 16 as seen in FIG. 2). In some instances, that internal volume may be reduced if, e.g., a vacuum is applied to reduce the pressure within the internal volume to a level below atmospheric pressure.

The port body 20 may be formed of a variety of different materials, although it may be preferred that the body 20 be fluid impermeable (outside of any passages formed therethrough). It may also be preferred that the body 20 be flexible such that it may at least somewhat conform to a body surface to which the port body 20 is attached.

Figure 3:
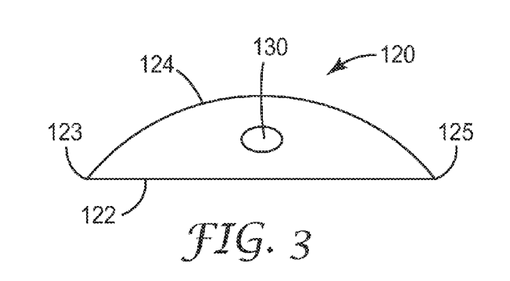
FIG. 3 is a side elevational view of an alternative port body that may be used in connection with the present invention.
Figure 4:
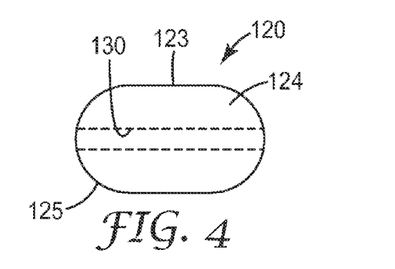
FIG. 4 is a top plan view of the port body of FIG. 3.

The port body 20 may preferably be in a form such that the upper surface 24 and the lower surface 22 meet at two opposing edges 23 and 25 that extend (in the depicted embodiment) from the external surface 28 to the internal surface 29. Although the embodiment depicted in FIGS. 1 & 2 includes two distinct edges 23 and 25, in some embodiments, the two opposing tapered edges may be locations on a continuous edge that extends along a curved path around a port body (see, e.g., port body 220 in FIGS. 3 & 4 below). In either case, the two opposing tapered edges are located on opposite sides of the port body over which a backing is located.

Although the edges of the depicted port body 20 are relatively smooth, other edge designs may be used, e.g., sawtooth patterns, wavy patterns (e.g., sinusoidal, etc.).

It may be preferred that the upper surface 24 and the lower surface 22 form an internal angle of less than 90 degrees along the tapered edges 23 and 25 of the port body 20. In some embodiments, the internal angle formed by the upper surface 24 and the lower surface 22 may preferably be 75 degrees or less. The internal angle may alternatively be characterized as an acute angle. If the port body used in connection with the medical dressings does not have a straight edges such as that depicted in FIG. 1, the internal angle referred to herein is preferably measured within a cross-section of the port body that is taken in a plane that extends between the junctions between the backing 12 and the port body 20 on the opposing edges 23 and 25, with the plane being oriented normal to the backing 12.

The tapered edges 23 and 25 over which the backing 12 is attached preferably provide a relatively smooth transition from the port body 20 to a body surface to which the dressing is attached. As depicted in FIG. 2, the liner 16 serves as a representative body surface to illustrate this potential advantage of the dressings of the present invention. The smooth transition from the port body 20 to the liner/body surface 16 preferably allows a user to attach the dressing 10 in a manner that seals the backing 12 and the port body 20 such that infiltration of foreign materials, air, etc. into a wound covered by the dressing 10 is substantially impeded or prevented.

Among the other optional features depicted in connection with the embodiment depicted in FIGS. 1 and 2 is that the port body 20 may extend past a perimeter of the backing 12 such that a portion of the upper surface 24 of the port body 22 is not covered by the backing 12. In the depicted embodiment, the port body 20 has an arcuate upper surface 24 (although as described herein, other configurations may be used). More particular, the port body 20 depicted in FIGS. 1 and 2 may be described as the section (e.g., a semicircular section) of a circular cylinder which may be more particularly described as a right circular cylinder in which the end faces (the external surface 28 and the internal surface 29) may be are flat (e.g., substantially planar) surfaces.

Still another optional feature depicted in FIGS. 1 & 2, is the carrier 18 which may be particularly useful if the backing 12 is flexible as described herein. The carrier 18 may preferably include tabs 19 that can facilitate handling of the dressing 10 during placement on a patient. The carrier 18 may preferably be provided in the shape of frame that extends around a significant portion of the perimeter of the backing 12. In the depicted embodiment, the carrier 18 includes an optional intermediate separation line 17 such that the inner and outer portions of the carrier 18 may be removed separately from each other. Some potentially suitable examples of carriers (such as carrier 18) that may be used in connection with the present invention may be found in, e.g., U.S. Pat. Nos. 6,169,224; 5,088,483; and 4,598,004.

Although the port body 20 depicted in connection with FIGS. 1 & 2 may be in the form of a section or portion of a right circular cylinder, the port bodies used in connection with the present invention may take on a variety of different shapes. Some examples of potential alternately shaped port bodies are depicted in connection with the FIGS. 3-6 (although these are only some examples of the potential alternate shapes). The port body 120 depicted in FIGS. 3 & 4 (with FIG. 3 being a side elevational view and FIG. 4 being a top plan view) includes lower surface 122 and an upper surface 124, with a passage 130 extending through the port body 120. The port body 120 has a generally elongated, oval-like shape with the lower surface 122 and the upper surface 124 meeting along tapered edges 123 and 125 to provide a smooth transition between the port body 120 and a body surface (not shown) to which the port body 120 and its associated backing are attached.

Figure 5:
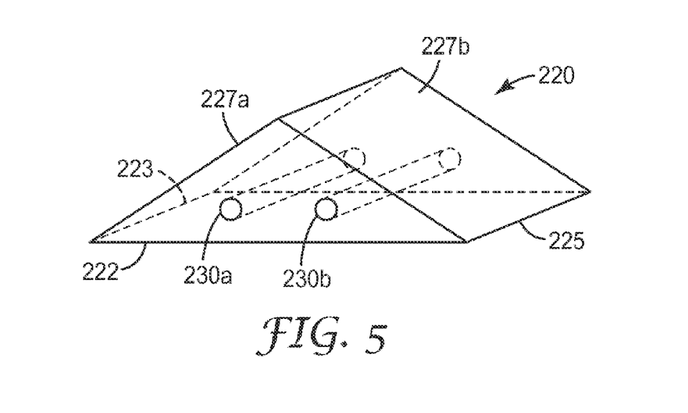
FIG. 5 is a perspective view of another alternative port body that may be used in connection with the present invention.

Another example of an alternate shape for a port body is depicted in FIG. 5 in which the port body 220 includes a lower surface 222 and an upper surface that includes two faces 227a and 227b. The two faces 227a and 227b, along with the lower surface 222, give the port body 220 the shape of a triangular prism with two tapered edges 223 and 225 to provide a smooth transition between the port body 220 and a body surface (not shown) to which the port body 220 and its associated backing are attached. The port body 220 also includes two passages 230a and 230b formed therethrough to provide access to an internal volume when the port body 220 is used in connection with a medical dressing as described herein.

Figure 6:
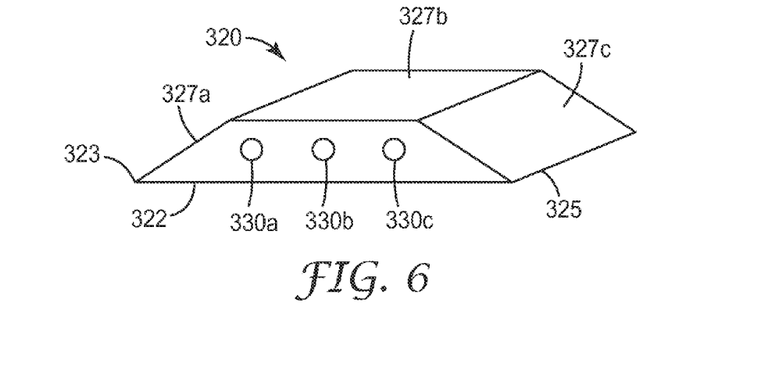
FIG. 6 is a perspective view of another alternative port body that may be used in connection with the present invention.

Still another example of an alternate shape for a port body is depicted in FIG. 6 in which the port body 320 includes a lower surface 322 and an upper surface that includes three faces 327a, 327b, and 327c. The three faces 327a, 327b, and 327c, along with the lower surface 322, give the port body 320 the shape of a prism with bases in the form of a trapezoid. The port body 320 includes two tapered edges 323 and 325 to provide a smooth transition between the port body 320 and a body surface (not shown) to which the port body 320 and its associated backing are attached. The port body 320 also includes three passages 330a, 330b, and 330c formed therethrough to provide access to an internal volume when the port body 320 is used in connection with a medical dressing as described herein.

The various alternate port body shapes depict a variety of different features that may be included in the port bodies of the present invention. Generally, however, it may be preferred that the lower surface be flat such that the port body can form an acceptable seal with a body surface to which the port body is attached. The upper surface may include a variety of differently shaped features, although it is preferred that the upper surface meet the lower surface along two opposing tapered edges so that a smooth transition between the port body, the backing, and the body surface can be obtained. The upper surface may include only flat surfaces (as in FIGS. 5 & 6), in which case the port body may be described as having a prismatic shape In other embodiments, the upper surface may include only curved surfaces (as in FIGS. 3 & 4). In still other embodiments, the upper surface may include both flat and curved surfaces (as in FIGS. 1 & 2).

Figure 7:
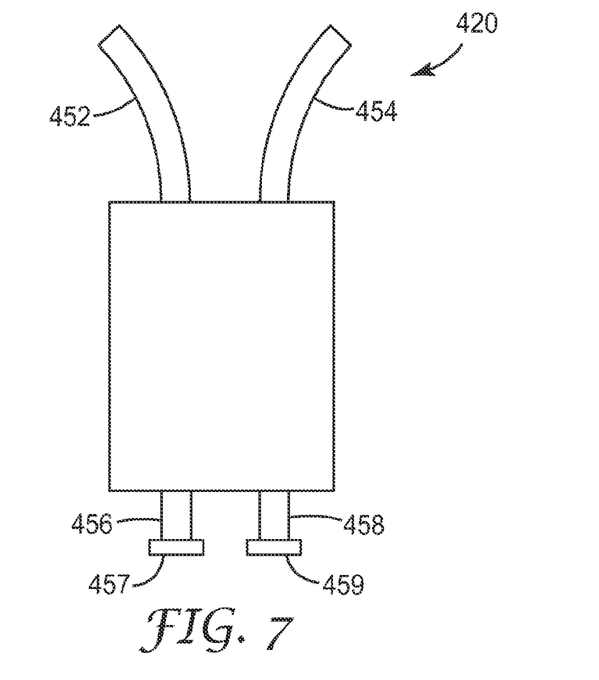
FIG. 7 is a plan view of another medical dressing according to the present invention (with tubes).

Yet another embodiment of a port body 420 is depicted in FIG. 7. The port body 420 includes extensions 452 and 454 (e.g., tubes or other structures) extending from a pair of internal openings (not seen in FIG. 7). Although two extensions are depicted in FIG. 7, it should be understood that port bodies used in connection with the present invention may include only one such extension or more than two extensions. Typically, each extension will be connected to a single internal opening in the port body 420, although other arrangements are also possible. The extensions 452 and 454 may be used to assist in the movement of fluid into and/or out of the internal volume defined by the medical dressings of the present invention (as described herein). The extensions may take a variety of configurations. For example, the extensions used in connection with the present invention may be perforated, porous, etc. (e.g., similar to the tubes used in connection with Jackson Pratt wound drains, etc.). In other alternatives, the extensions may have more complex longitudinal shapes such as those disclosed in U.S. Pat. No. 4,398,910 (Blake et al.).

Also depicted in FIG. 7 are extensions 456 and 458 that extend from the external openings in the port body 420. The extensions 456 and 458 may be used to connect to, e.g., pumps, fluid sources (e.g., oxygen, saline, etc.) that may be employed to deliver fluids into and/or out of the internal volume defined by the medical dressing as described herein. The extensions 456 and 458 may, respectively, include a fitting 457 and 459 that can facilitate leakproof connections. For example, the fittings 457 & 459 may be used in a quick connect configuration such as, e.g., a Luer Lock type connection (although other connectors may also be used).

In some embodiments, the extensions 452 and 454 extending from the internal openings may be unitary with the extensions 456 and 458 that extend from the external openings—in other words, the extension 452 may be unitary with extension 456 and extension 454 may be unitary with tube 458. Alternatively, the different extension may be separate and distinct articles that are attached to the port body 420.

Figure 8:
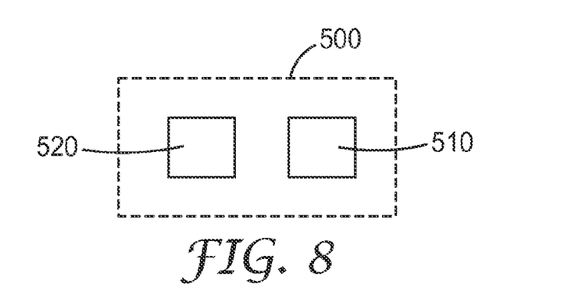
FIG. 8 is a block diagram of components that may be supplied in one exemplary embodiment of a medical dressing kit according to the present invention.

Although the medical dressings of the present invention may be provided with the port body attached to the backing, in some embodiments, the present invention may be provided in the form of a kit in which one or more port bodies are provided separately from one or more backings FIG. 8 depicts such a kit 500 in which a port body 520 is provided separately from a medical dressing 510. Any such kit may preferably be provided in a sealed package such that the cleanliness and sterility of the different components can be protected during transport and storage.

In using such a kit, the port body (or bodies) may be placed on the skin of a patient followed by placement of a backing over the port body such that in internal volume is created by the port body and the backing. Alternatively, the user may assemble (e.g., attach) the port body to a backing before placing either the port body or the backing on a patient.

The kits of the present invention may also include other materials such as, e.g., wound packing materials. Some potentially suitable examples of wound packing materials may include fully or partially reticulated foam, fabric (e.g., gauze, woven, knit, or nonwoven materials), particulate materials, etc. that may be placed in a wound fill the internal volume.

The port bodies of the medical dressings of the present invention may preferably be placed across the periwound area (the edge of the wound) such the internal openings in the port bodies are in fluid communication with the internal volume defined by the dressing (and in which any wound packing material may be located).

When used, the passages formed through the port bodies may be used to control the environment within the internal volume defined by the dressing over the wound by presenting the opportunity to remove fluid from and/or deliver fluid to the interior volume (and, thus, the wound covered by the dressing). The fluids removed from internal volumes created over wounds by the medical dressing of the present invention may include air or other gases (e.g., oxygen, nitric oxide, ozone, etc.) and/or liquids (e.g., wound exudate, saline, etc.). In some instances, removal of gases within the internal volume may preferably provide a negative or reduced pressure environment in which the gas pressure within the internal volume is below ambient atmospheric pressure (i.e., pressure outside of the internal volume). As a result, the medical dressing of the present invention may be used to provide negative or reduced pressure wound therapy.

The use of more than one port body and/or more than one passage through a single port body may offer the opportunity to both remove fluids from and deliver fluids to the internal volume created by a dressing of the present invention. Fluids delivered to the internal volume may include gases (e.g., oxygen, nitric oxide, ozone, etc.) and/or liquids (e.g., saline, water, etc.). Particulates may, in some instances, also be delivered to the internal volume if, e.g., they are entrained within a fluid delivered through a passage.

In some instances, a passage through a port body may be used to deliver one or more active agents to the internal volume (and, thus, the wound covered by the dressing). The active agents may be provided as a fluid and/or may be carried within a fluid that is delivered to the internal volume. Some potentially suitable active agents may include, e.g., antimicrobials, antibiotics, analgesics, healing factors such as vitamins, growth factors, nutrients and the like.

If delivered, an active agent (or agents) could be supplied continuously or intermittently. For example, an active agent could be delivered to the internal volume and allowed to remain in place (i.e., resident) for a selected period of time (e.g., several hours) followed by the delivery of a second active agent. The initial active agent could be removed before delivery of the second agent or it could be allowed to remain in place. Alternatively, the internal volume could be rinsed with, e.g., saline or another flushing solution before delivery of the second agent. If two passages are provided into the internal volume, the delivery and removal of the fluids may coordinated between the two or more passages to improve efficacy of the treatment regime depending on the different active agents and the desire to provide negative pressure wound therapy and/or gas therapy to a wound.

The following discussions will provide some non-limiting examples as to the construction of the various features that may be used in connection with the medical dressings of the present invention.

Port Bodies:

It may be preferred that the port bodies used in connection with the present invention be manufactured of materials that provide a fluid barrier to limit or effectively prevent the passage of liquids or gases therethrough (outside of the passages intentionally provided through the port bodies). The materials used for the port bodies may preferably be relatively resilient or flexible to assist in conforming and adhering to a body site. Examples of some potentially suitable materials may include, e.g., plasticized PVC, polyurethanes, silicones, block copolymer elastomers (e.g., block copolymer elastomers available under the trade designation KRATON), polyolefins (including metallocene polyolefins), polyamides (e.g., polyester block amides available under the trade designation PEBAX), elastomeric polyesters (including elastomeric Polyesters available under the trade designation HYTREL), etc. Thermoset elastomers may also be suitable—such as ethylene propylene diene monomers (EPDM), butyl rubbers, nitrile rubbers, natural rubbers, neoprenes, etc.

In some embodiments, the port bodies may be manufactured as composite articles, e.g., a collection of two or more components such as a resilient base and a less resilient upper portion, etc.

Port bodies of the present invention may be formed by any suitable technique. It may be preferred to use manufacturing processes that can efficiently produce port body structures such as, e.g., melt extrusion. Other potential manufacturing techniques may include, e.g., injection molding, insert molding, etc. In other embodiments, the port bodies may be formed in a molding operation in which a reaction occurs, such as, e.g., a two-part polyurethane or silicone reaction, free radical cure reaction, etc.

Figure 9:
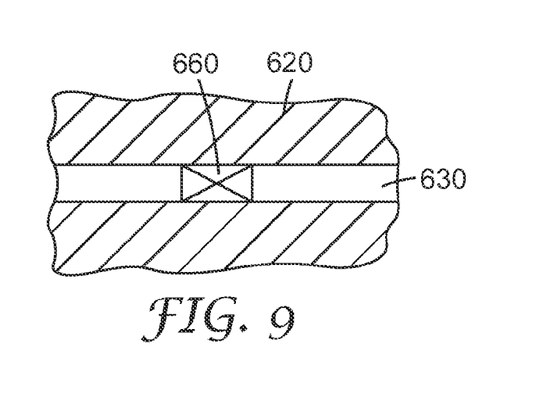
FIG. 9 is a cross-sectional view of a passage including a valve to control fluid flow through the passage.

The port bodies used in connection with the present invention may include one or more valves to control fluid flow through the passages formed in the port bodies. A cross-sectional diagram depicting a valve 660 located within a passage 630 in a port body 620 is provided as FIG. 9. Although depicted as being located within the passage 630, it should be understood that the valve 660 may be located at either end of the passage 630 such that the valve 660 controls flow into the passage 630. Alternatively, the valve(s) can be placed in extensions such as 452, 454, 456 and 458 of FIG. 7.

The valves used in connection with the invention may preferably be self-closing one-way or unidirectional valves that allow flow in one direction and restrict flow in the opposite direction, although other valves may alternatively be used. Some potentially suitable self-closing one-way valves may include, e.g., duckbill valves, button valves, umbrella valves, spring-loaded ball valves, etc.

In some embodiments, it may be preferred that the one-way valves be arranged such that they operate as exhaust valves that permit fluid flow through the passage out of the internal volume and restrict fluid flow through the passage into the internal volume. By using a one-way exhaust valve, it may be possible to intermittently remove fluid from the internal volume created by a dressing of the present invention and to retain any reduced or negative pressure condition created by the fluid removal in between removal events.

In some embodiments, it may be preferred to provide a feed valve that can be used to deliver fluid into the internal volume through a passage in a port body. Such a feed valve may or may not be a one-way valve. If the feed valve is a one-way valve, it may be arranged to permit fluid flow through the passage into the internal volume and restrict fluid flow through the passage out of the internal volume.

Backings:

The medical dressings of the present invention are useful in connection with any conformable backing that preferably provides a barrier to the passage of liquids and at least some gases. Representative backings may include polymeric films and other familiar backing materials. The preferred backing materials are translucent or transparent polymeric films.

It may be preferred that the backings used in connection with the present invention be high moisture vapor permeable film backings Issued U.S. Pat. Nos. 3,645,835 and 4,595,001 describe methods of making such films and methods for testing their permeability. It may be preferred that the film (and any adhesive used thereon as described herein) transmit moisture vapor at a rate equal to or greater than human skin. Preferably, the adhesive-coated film transmits moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backings may also preferably be conformable to anatomical surfaces. As such, when the backing is applied to an anatomical surface, it conforms to the surface even when the surface is moved. The preferred backing may also be conformable to animal anatomical joints. When the joint is flexed and then returned to its unflexed position, the backing stretches to accommodate the flexion of the joint, but is resilient enough to continue to conform to the joint when the joint is returned to its unflexed condition. A description of this characteristic of backings can be found in issued U.S. Pat. Nos. 5,088,483 and 5,160,315. As discussed, particularly preferred backings may be elastomeric polyurethane, polyester, or polyether block amide films. These films combine the desirable properties of resiliency, high moisture vapor permeability, and transparency.

Commercially available examples of potentially suitable backing materials may include the thin polymeric film backings sold under the trade designations TEGADERM (3M Company), BIOSITE (Johnson & Johnson Company), OPSITE (Smith & Nephew), etc. Many other backings may also be used, including those commonly used in the manufacture of surgical incise drapes (e.g., incise drapes manufactured by 3M Company under the trade designation STERIDRAPE and IOBAN), etc.

Carriers/Delivery Systems:

In some instances, the backings used in the medical dressings of the present invention may be so flexible and supple such that when a release liner is removed from the backing, the backing may tend to fold and adhere to itself, interfering with the smooth, aseptic application of the dressing to a patient's skin.

Various delivery systems have been proposed to address this problem such as those disclosed in U.S. Pat. No. 4,485,809; U.S. Pat. No. 4,600,001; and EPO Publication No. 0 051 935. Carrier-type delivery systems such as those described in U.S. Pat. No. 6,685,682 offer an alternative delivery system for use with conformable backings.

Alternative carriers and/or delivery systems may include frames, handles, stiffening strips, etc. as disclosed in issued U.S. Pat. Nos. 6,742,522; 5,979,450; 6,169,224; 5,088,483; 4,598,004; D 493,230; etc. Still another potentially suitable delivery system may be described in U.S. Patent Application No. US 2007/0156075 A1. In some instances, the backings can be delivered linerless as described in, e.g., U.S. Pat. No. 5,803,086.

Pressure Sensitive Adhesives:

The pressure sensitive adhesives that may preferably be used in the medical dressings and the port bodies of the present invention may include adhesives that are typically applied to the skin such as the acrylate copolymers described in U.S. Pat. No. RE 24,906, particularly a 96:4 iso-octyl acrylate:acrylamide copolymer. Another example may include a 70:15:15 isooctyl acrylate: ethyleneoxide acrylate: acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

The pressure sensitive adhesives may preferably transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001.

Release Liners:

Release liners that may be suitable for use in the medical dressing of the present invention can be made of supercalendered kraft paper, glassine paper, polyethylene, polypropylene, polyester or composites of any of these materials. The liners are preferably coated with release agents such as hydrocarbons, fluorochemicals, silicones, or combinations thereof. For example, U.S. Pat. No. 4,472,480 describes low surface energy perfluorochemical liners. The liners may preferably be in the form of papers, polyolefin films, polyolefin coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Florchheim, (Florchheim, Germany). Another potential liner is silicone coated (1630) low density polyethylene available from Huhtamaki.

The selection of a specific release liner may be made in conjunction with the selection of a pressure sensitive adhesive. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

The complete disclosure of the patents, patent documents, and publications cited herein are incorporated by reference in their entirety as if each were individually incorporated (although conflicts between any such disclosures and the descriptions explicitly provided herein should be resolved in favor of this document).

Exemplary embodiments of this invention are discussed and reference has been made to possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A medical dressing comprising:
a port body comprising a lower surface and an upper surface, wherein the lower surface and the upper surface meet along two opposing tapered edges, wherein the upper surface and the lower surface of the port body form an internal angle of less than 90 degrees along the tapered edges of the port body;
a passage extending through the port body from an external opening to an internal opening;
pressure sensitive adhesive located on the lower surface of the port body; and,
a backing attached to the upper surface of the port body, the backing extending over the upper surface between the two opposing tapered edges of the port body, wherein the external opening is located proximate the edge of the backing such that, when the backing and the lower surface of the port body are attached to a body surface, the internal opening opens into an internal volume defined at least in part by the backing, the port body and the body surface,
wherein the port body comprises a one-way exhaust valve that is located within the passage extending through the port body and that is arranged to permit flow of a fluid through the passage out of the internal volume and to restrict flow of the fluid through the passage into the internal volume.

2. A medical dressing according to claim 1, wherein the internal angle formed by the upper surface and the lower surface of the port body along the tapered edges of the port body is 75 degrees or less.

3. A medical dressing according to claim 1, wherein the port body extends outside of a perimeter of the backing, so that a portion of the upper surface of the port body is not covered by the backing outside of the perimeter of the backing.

4. A medical dressing according to claim 1, wherein the backing is adhesively attached to the upper surface of the port body.

5. A medical dressing according to claim 1, wherein the port body further comprises an internal extension connected to the internal opening.

6. A medical dressing according to claim 1, wherein the port body further comprises an external extension connected to the external opening.

7. A medical dressing according to claim 1, wherein the medical dressing further comprises a feed valve arranged to permit a selected fluid to be delivered into the internal volume.

8. A medical dressing according to claim 7, wherein the feed valve is located within an auxiliary port body, and wherein the auxiliary port body comprises:
a flat lower surface and an upper surface, wherein the lower surface and the upper surface meet along two opposing tapered edges, wherein the upper surface and the lower surface of the auxiliary port body form an internal angle of less than 90 degrees along the tapered edges of the auxiliary port body;
a passage extending through the auxiliary port body from an external opening to an internal opening;
pressure sensitive adhesive located on the lower surface of the auxiliary port body; and
wherein the backing is attached to the upper surface of the auxiliary port body, the backing extending over the upper surface between the two opposing tapered edges of the auxiliary port body, wherein the external opening is located proximate the edge of the backing such that, when the backing and the lower surface of the auxiliary port body are attached to a body surface, the internal opening opens into the internal volume.

9. A medical dressing according to claim 1, wherein the upper surface of the port body comprises a curved surface.

10. A medical dressing according to claim 1, wherein the upper surface of the port body comprises a section of a circular cylinder.

11. A medical dressing according to claim 1, wherein the port body comprises a solid body with the passage extending therethrough.

12. A medical dressing according to claim 1, further comprising a secondary passage extending through the port body between a secondary external opening and a secondary internal opening, wherein, when the backing and the lower surface of the port body are attached to a body surface, the secondary internal opening opens into the internal volume.

13. A medical dressing according to claim 1, wherein the passage extending through the port body does not contain an elongated member inserted therethrough; and, wherein the dressing is configured so that when the backing and the lower surface of the port body are attached to a body surface, the internal volume does not contain an elongated member extending thereinto from within the passage extending through the port body.

14. A medical dressing according to claim 1, wherein the backing comprises a polymeric film backing.

15. A medical dressing according to claim 1, wherein the medical dressing further comprises pressure sensitive adhesive located on a lower surface of the backing, wherein the lower surface of the backing faces the upper surface of the port body and is adhesively attached thereto by the pressure sensitive adhesive.

16. The medical dressing according to claim 15, further comprising a release liner covering the pressure sensitive adhesive on the lower surface of the port body and the pressure sensitive adhesive on the lower surface of the backing.

17. The medical dressing according to claim 1, wherein the one-way exhaust valve is located entirely within the passage extending through the port body.

18. A method of treating a wound, the method comprising:
applying a medical dressing over a wound, wherein the medical dressing comprises:
a port body comprising a lower surface and an upper surface, wherein the lower surface and the upper surface meet along two opposing tapered edges, wherein the upper surface and the lower surface of the port body form an internal angle of less than 90 degrees along the tapered edges of the port body;
a passage extending through the port body from an external opening to an internal opening;
pressure sensitive adhesive located on the lower surface of the port body; and a backing attached to the upper surface of the port body, the backing extending over the upper surface between the two opposing tapered edges of the port body, wherein the external opening is located proximate the edge of the backing;

wherein the lower surface of the port body is attached to a body surface surrounding the wound, and wherein the internal opening opens into an internal volume defined at least in part by the backing, the port body, the body surface, and the wound, and wherein the port body comprises a one-way exhaust valve that is located within the passage extending through the port body and that is arranged to permit flow of a fluid through the passage out of the internal volume and to restrict flow of the fluid through the passage into the internal volume;

and, removing fluid from the internal volume through the passage extending through the port body.

19. A method according to claim 18, wherein the fluid removed from the internal volume comprises air such that the pressure within the internal volume is below atmospheric pressure outside of the internal volume.

20. A method according to claim 18, wherein the fluid removed from the internal volume comprises wound exudate from the wound.

21. A method according to claim 18, wherein the medical dressing further comprises a feed valve arranged to permit a selected fluid to be delivered into the internal volume, and wherein the method further comprises delivering the selected fluid into the internal volume through the feed valve.

22. A method according to claim 21, wherein the feed valve is located within an auxiliary port body, and wherein the auxiliary port body comprises:

a lower surface and an upper surface, wherein the lower surface and the upper surface meet along two opposing tapered edges, wherein the upper surface and the lower surface of the auxiliary port body form an internal angle of less than 90 degrees along the tapered edges of the auxiliary port body;

a passage extending through the auxiliary port body from an external opening to an internal opening;

pressure sensitive adhesive located on the lower surface of the auxiliary port body; and wherein the backing is attached to the upper surface of the auxiliary port body, the backing extending over the upper surface between the two opposing tapered edges of the auxiliary port body, wherein the external opening is located proximate the edge of the backing such that the internal opening opens into the internal volume.

23. A method according to claim 18, wherein the internal angle formed by the upper surface and the lower surface of the port body along the tapered edges of the port body is 75 degrees or less.

24. A method according to claim 18, wherein the port body extends outside of a perimeter of the backing, so that a portion of the upper surface of the port body is not covered by the backing outside of the perimeter of the backing.

25. A method according to claim 18, wherein the backing is adhesively attached to the upper surface of the port body.

26. A method according to claim 18, wherein the port body further comprises an internal extension connected to the internal opening.

27. A method according to claim 18, wherein the port body further comprises an external extension connected to the external opening.

28. A method according to claim 18, wherein the upper surface of the port body comprises a curved surface.

29. A method according to claim 18, wherein the upper surface of the port body comprises a section of a circular cylinder.

30. A method according to claim 18, wherein the port body comprises a solid body with the passage extending therethrough.

31. A method according to claim 18, further comprising a secondary passage extending through the port body between a secondary external opening and a secondary internal opening, wherein, when the backing and the lower surface of the port body are attached to a body surface, the secondary internal opening opens into the internal volume.

32. A method according to claim 18, wherein the passage extending through the port body does not contain an elongated member inserted therethrough and wherein the dressing is configured so that when the backing and the lower surface of the port body are attached to a body surface the internal volume does not contain an elongated member extending thereinto from within the passage extending through the port body.

33. A method according to claim 18, wherein the backing comprises a polymeric film backing.

34. A method according to claim 18, wherein the medical dressing further comprises pressure sensitive adhesive located on a lower surface of the backing, wherein the lower surface of the backing faces the upper surface of the port body and is adhesively attached thereto by the pressure sensitive adhesive.

35. A method according to claim 18, wherein the one-way exhaust valve is located entirely within the passage extending through the port body.

* * * * *